(12) United States Patent
Todd et al.

(10) Patent No.: US 9,375,544 B2
(45) Date of Patent: *Jun. 28, 2016

(54) FACE MASK

(71) Applicant: RIC INVESTMENTS, LLC, Wilmington, DE (US)

(72) Inventors: Jonathan P. Todd, Murrysville, PA (US); Christopher James McCracken, Harrison City, PA (US); Robert Hieber, Export, PA (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 109 days.

This patent is subject to a terminal disclaimer.

(21) Appl. No.: 14/048,120

(22) Filed: Oct. 8, 2013

(65) Prior Publication Data
US 2014/0034057 A1 Feb. 6, 2014

Related U.S. Application Data

(63) Continuation of application No. 12/742,950, filed as application No. PCT/IB2008/054722 on Nov. 11, 2008, now Pat. No. 8,573,217.

(60) Provisional application No. 60/987,843, filed on Nov. 14, 2007.

(51) Int. Cl.
*A61M 11/00* (2006.01)
*A61M 16/06* (2006.01)
(Continued)

(52) U.S. Cl.
CPC ........... *A61M 16/06* (2013.01); *A61M 16/0415* (2014.02); *A61M 16/0858* (2014.02); *A61M 16/1065* (2014.02); *A61M 15/009* (2013.01); *A61M 16/0463* (2013.01);
(Continued)

(58) Field of Classification Search
CPC ............ A61M 16/06; A61M 16/0816; A61M 16/1065; A61M 15/009; A61M 16/0463; A61M 16/0683; A61M 16/1045; A61M 16/16; A61M 16/208; A61M 2016/0027; A61M 2205/0244; A61M 2209/06; A61M 2230/432; A61M 16/0415; A61M 16/0858
USPC ............. 128/202.27, 205.11, 205.25, 205.24, 128/911, 206.28, 207.12, 206.21
See application file for complete search history.

(56) References Cited

U.S. PATENT DOCUMENTS

| 3,680,555 A | 8/1972 | Warncke |
| 4,177,381 A | 12/1979 | McClatchie |

(Continued)

FOREIGN PATENT DOCUMENTS

| WO | WO03022329 | 3/2003 |
| WO | WO2004096332 A1 | 11/2004 |

(Continued)

*Primary Examiner* — Steven Douglas
(74) *Attorney, Agent, or Firm* — Michael W. Haas

(57) ABSTRACT

A mask assembly is provided for delivering gas to a patient that includes a mask body and a breathing circuit interface. The mask body includes an opening for reception of the gas and includes a seal structure for sealingly engaging with the face of the patient and surrounding at least the nose and mouth of the patient. The breathing circuit interface includes a first portion rotatably connected with the mask body and a second portion that is constructed and arranged to releasably connect with a conduit for delivering the gas to the patient through the opening.

10 Claims, 18 Drawing Sheets

(51) Int. Cl.

| | |
|---|---|
| A61M 15/00 | (2006.01) |
| A61M 16/04 | (2006.01) |
| A61M 16/08 | (2006.01) |
| A61M 16/10 | (2006.01) |
| A61M 16/16 | (2006.01) |
| A61M 16/20 | (2006.01) |
| A61M 16/00 | (2006.01) |

(52) U.S. Cl.
CPC ....... *A61M 16/0683* (2013.01); *A61M 16/0816* (2013.01); *A61M 16/1045* (2013.01); *A61M 16/16* (2013.01); *A61M 16/208* (2013.01); *A61M 2016/0027* (2013.01); *A61M 2205/0244* (2013.01); *A61M 2209/06* (2013.01); *A61M 2230/432* (2013.01)

(56) References Cited

U.S. PATENT DOCUMENTS

| | | |
|---|---|---|
| 4,692,621 A | 9/1987 | Passaro |
| 4,859,858 A | 8/1989 | Knodle |
| 4,859,859 A | 8/1989 | Knodle |
| 4,914,720 A | 4/1990 | Knodle |
| 4,971,051 A | 11/1990 | Toffolon |
| 5,243,971 A | 9/1993 | Sullivan |
| 5,282,473 A | 2/1994 | Braig |
| 5,540,223 A | 7/1996 | Starr |
| 5,616,923 A | 4/1997 | Rich |
| 5,647,335 A | 7/1997 | Scheurenbrand |
| 5,647,355 A | 7/1997 | Starr |
| 5,647,357 A | 7/1997 | Barnett |
| 5,932,877 A | 8/1999 | Braig |
| 5,937,851 A | 8/1999 | Serowski |
| 6,397,847 B1 | 6/2002 | Scarberry |
| 6,402,697 B1 | 6/2002 | Calkins |
| 6,467,483 B1 | 10/2002 | Kopacko |
| 6,513,519 B2 | 2/2003 | Gallem |
| 6,851,425 B2 | 2/2005 | Jaffre |
| 7,255,106 B2 | 8/2007 | Gallem |
| 7,360,538 B2 | 4/2008 | Flynn |
| 7,874,292 B2 | 1/2011 | Smith |
| 7,909,035 B2 | 3/2011 | Thornton |
| 8,061,355 B2 | 11/2011 | Jaffre |
| 8,573,217 B2 * | 11/2013 | Todd et al. ............... 128/207.12 |
| 2002/0174866 A1 | 11/2002 | Orr |
| 2007/0044804 A1 | 3/2007 | Matula |

FOREIGN PATENT DOCUMENTS

| | | |
|---|---|---|
| WO | WO2005063326 A1 | 7/2005 |
| WO | WO2007048174 A1 | 5/2007 |

* cited by examiner

＃ FACE MASK

CROSS-REFERENCE TO RELATED APPLICATIONS

This patent application is a Continuation under 35 U.S.C. §120/121 of U.S. patent application Ser. No. 12/742,950, filed Nov. 11, 2008, now U.S. Pat. No. 8,573,217, which claims the priority benefit under 35 U.S.C. §119(e) of U.S. Provisional Application No. 60/987,843 filed on Nov. 14, 2007, the contents of which are herein incorporated by reference.

BACKGROUND OF THE INVENTION

1. Field of the Invention

The present invention relates to therapeutic gas delivery systems and, more particularly, to a mask that forms a seal with a patient's face during gas delivery.

2. Description of the Related Art

One class of respiratory face mask assemblies can be of two different types: a single limb circuit type and a dual limb circuit type. For a single limb circuit, the face mask assembly typically includes a valve and an exhaust port, and, for a dual limb circuit, the face mask assembly typically does not include a valve but provides a valveless conduit instead. Other types of masks may also be useful for different applications. Thus, hospitals and other health care facilities typically stock several different types of face mask assemblies that are used for different applications. Cost and storage space considerations associated with stocking several different face mask assemblies can be significant.

SUMMARY OF THE INVENTION

One aspect of the present invention provides a mask assembly for providing gas to a patient. The mask assembly includes a mask body having an opening for reception of the gas and a breathing circuit interface. The mask body includes a seal structure for sealingly engaging with the face of the patient and surrounding at least the nose and mouth of the patient. The breathing circuit interface includes a first portion rotatably connected with the mask body and a second portion that is constructed and arranged to releasably connect with a conduit for delivering the gas to the patient through the opening.

Another aspect of the present invention provides a mask assembly for providing gas to a patient. The mask assembly includes a mask body having an opening for reception of the gas and a conduit. The mask body includes a seal structure for sealingly engaging with the face of the patient and surrounding at least the nose and the mouth of the patient, and a connecting portion. The conduit is releasably connected with the connecting portion of the mask body. The conduit includes a first connector portion which connects with the connecting portion, and a second connector portion that is constructed and arranged to connect with tubing, wherein the first connector portion includes a plurality of recesses at an interface with the connecting portion to allow exhaled gas to escape therethrough.

In yet another embodiment, the present invention provides a mask assembly kit for providing gas to a patient. The mask assembly kit includes a mask body having an opening for reception of the gas, a first, valveless conduit, and a second conduit containing a valve. The mask body includes a seal structure for sealingly engaging with the face of the patient and surrounding at least the nose and the mouth of the patient. Each of the conduits includes a first connector portion which connects with a connecting portion associated with the mask body, and a second connector portion constructed and arranged to connect with tubing. The connecting portion of the mask body is constructed and arranged to be selectively attached to the first connector portion of either the first conduit or the second conduit.

These and other aspects of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1A:
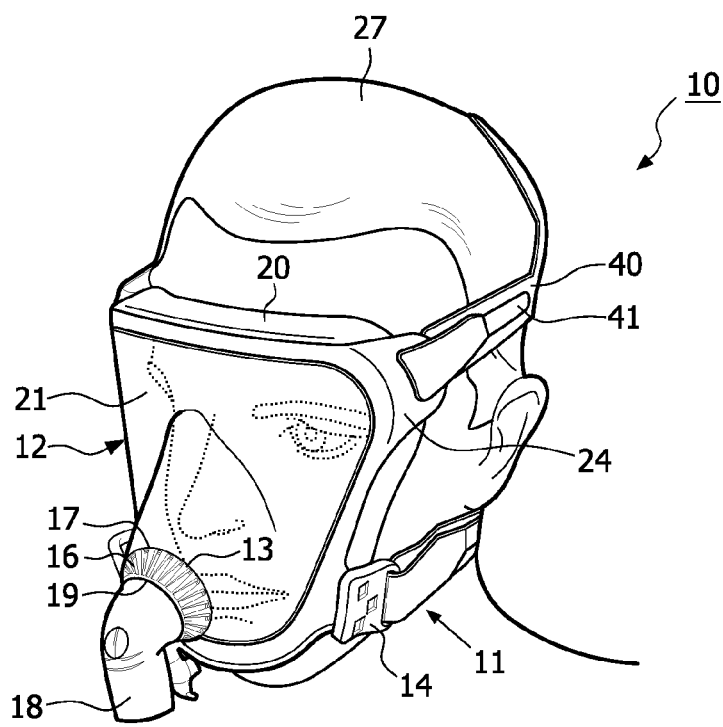
FIG. 1A is a perspective view of the mask assembly and patient's face in accordance with an embodiment of the present invention.

FIGS. 1A, 1B, 2 and 3 show a mask assembly 10 for use in a therapeutic gas delivery in accordance with an embodiment of the present invention. The mask assembly 10 may generally include a mask body 12 having an opening 13 for reception of gas. The mask body 12 includes a seal structure 20 for sealingly engaging with the face of the patient 27 in surrounding relation to at least the nose and mouth (and optionally the eyes) of the patient 27. The mask assembly 10, in one embodiment, also includes a breathing circuit interface 16 for connecting the mask body 12 with a pressurized breathing gas supply. As disclosed in more detail later, the breathing circuit interface 16 has a first portion 17 rotatably connected with the mask body 12 and a second portion 19 constructed and arranged to connect with a conduit 18 for delivering the gas to the patient 27 through the opening 13.

In an embodiment, the breathing circuit interface 16 and the conduit 18 connects the mask body 12, via a circuit tubing (not shown), to a source of gas (not shown), e.g., a blower, a CPAP machine, a ventilator or other suitable device, for providing breathing gas to the patient 27. As will be appreciated from further discussions herein, the second portion 19 of the breathing circuit interface 16 is releasably connected with the conduit 18 to enable different types of conduits 18 to be connected to the mask body 12. In addition, a rotatable or swivel connection between the breathing circuit interface 16 at the first portion 17 thereof with the mask body 12 allows the elbow shaped conduit 18 to rotate after connection to enable the conduit 18 to extend in any direction within a 360° of rotation for connecting with the tubing. It should be appreciated that for some purposes the breathing circuit interface 16 may also be considered to be part of the mask body 12.

Figure 3:
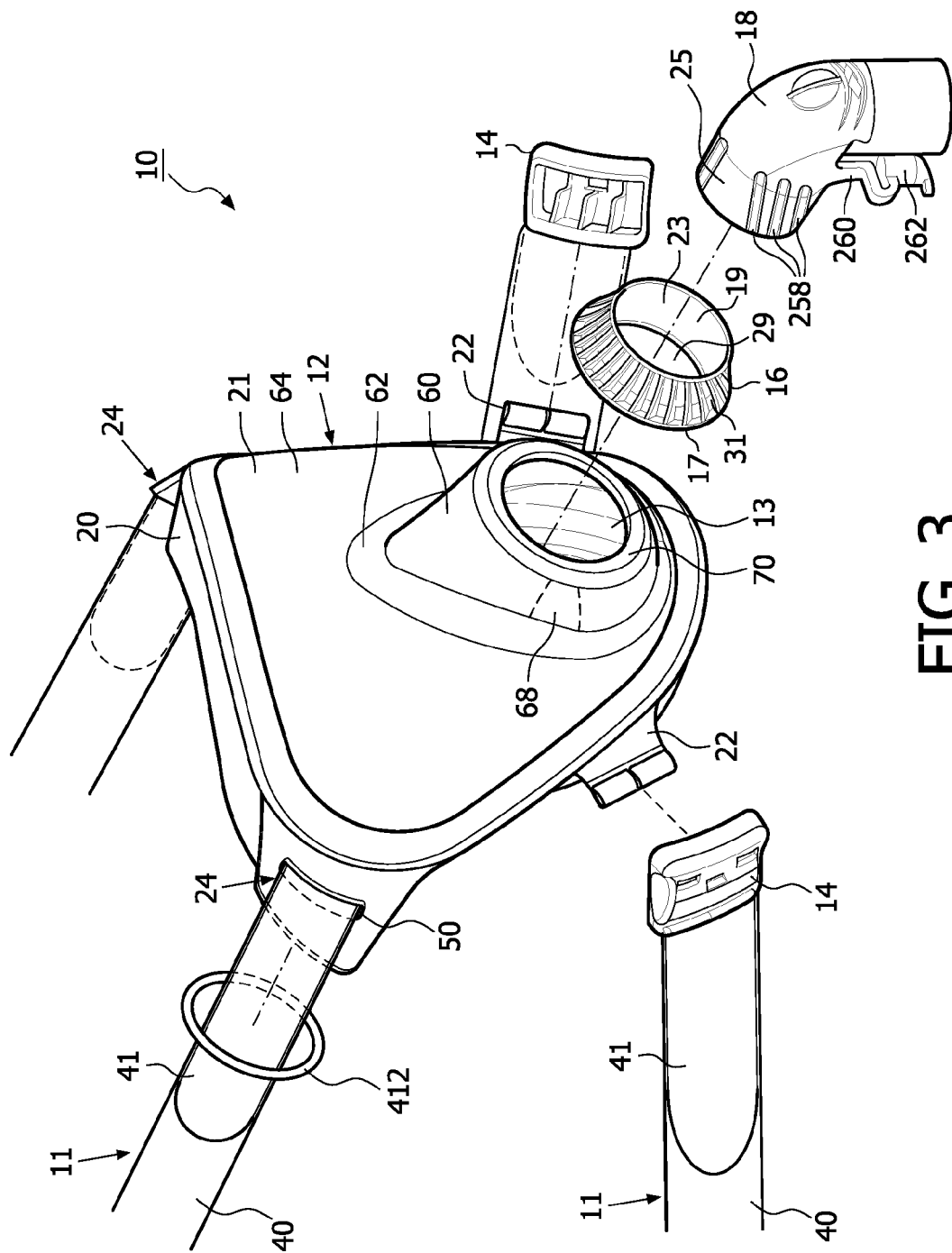
FIG. 3 is a perspective exploded view of a mask assembly in accordance with an embodiment of the present invention.

As shown in FIG. 3, the breathing circuit interface 16 has an annular configuration with a generally cylindrical inner surface 23 disposed about a central opening 29 therethrough. As will be appreciated from more detailed discussions later, the cylindrical inner surface 23 of the breathing circuit interface 16 is shaped and configured to provide a releasable friction fit with a generally cylindrical mating surface 25 of an appropriate conduit 18 that connects with tubing for receiving a breathable gas.

A plurality of radially outwardly extending ribs 31, which have an increasing thickness or radial dimension as they extend from the second portion 19 to the first portion 17 of the breathing circuit interface 16, are spaced at regular circumferential intervals. The ribs 31 are integrally formed as part of the outer surface of the breathing circuit interface 16. The plurality of ribs 31 located on the outer surface of the second portion 19 of the breathing circuit interface 16 provides the user 27 (or healthcare personnel) a grip to hold the breathing circuit interface 16 when connecting and disconnecting the conduit 18 to the breathing circuit interface 16. The ribs 31 also facilitate manual rotation of the breathing circuit interface 16.

In one embodiment, the mask body 12 includes a rigid portion 21, formed from a clear plastic material, and the aforementioned flexible peripheral seal structure 20. The flexible peripheral seal structure 20 is attached around the rigid portion 21 of the mask body 12. A protrusion 60 extends forwardly from a forward central portion of the rigid portion 21 of the mask body 12 and is shaped to accommodate the nose and the mouth of the patient 27. The protrusion 60 is generally pear shape about its periphery 62, where it meets the flatter parts 64 of the rigid portion 21 and includes the opening 13 located in the forwardmost portion thereof. The protrusion 60 includes a pair of indentations 68 located horizontally on either side of the opening 13. The pair of indentations 68 serves as finger receiving indentations and provides a region for an individual to grip the mask body 12 when placing and removing the mask body 12 on the patient's face.

Figure 2:
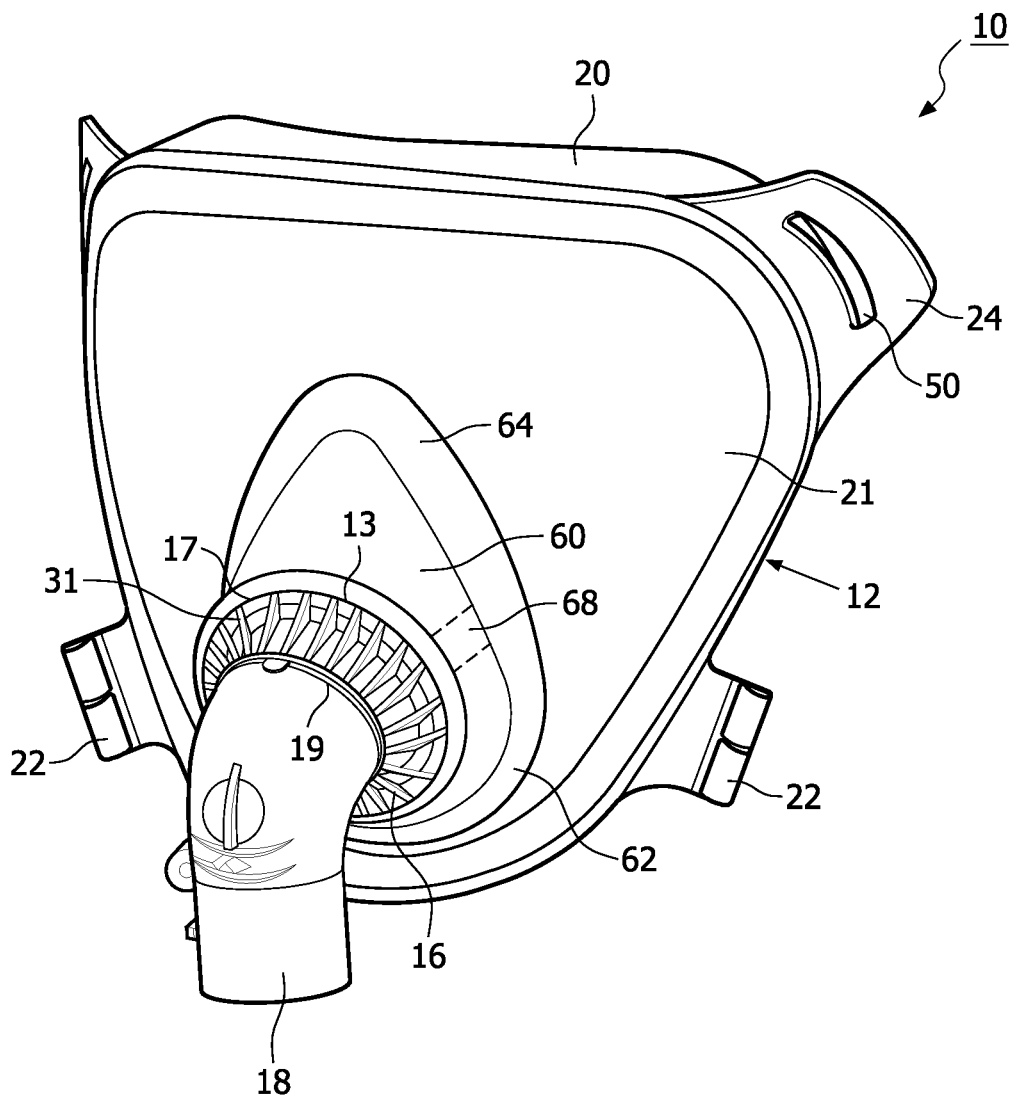
FIG. 2 is a perspective view of the mask assembly with an entrainment valve assembly in accordance with an embodiment of the present invention.

In one embodiment, the mask body 12 is adapted to be connected with headgear assembly 11 that can be used to mount the mask body 12 on the head of the patient 27. In an embodiment, a pair of headgear attachment clips 14 provided for interface and connection with lower headgear mounting strap portions 40 of the headgear assembly 11. A pair of headgear attachment members 22 is provided for connectably receiving the headgear attachment clips 14, and a pair of spaced upper headgear strap retaining tabs 24, each having an elongated opening 50 therethrough, is provided for receiving upper headgear mounting strap portions 40 of the headgear assembly 11. The pair of headgear retaining tabs 24 is disposed on the opposite upper sides of the rigid portion 21 of the mask body 12. The pair of headgear attachment members 22 is disposed on opposite, lower sides of the rigid portion 21 of the mask body 12. Each headgear retaining tab 24 is integrally formed with rigid portion 21 and extends outwardly from the flexible peripheral seal structure 20, as best seen in FIGS. 2 and 3.

Figure 4:
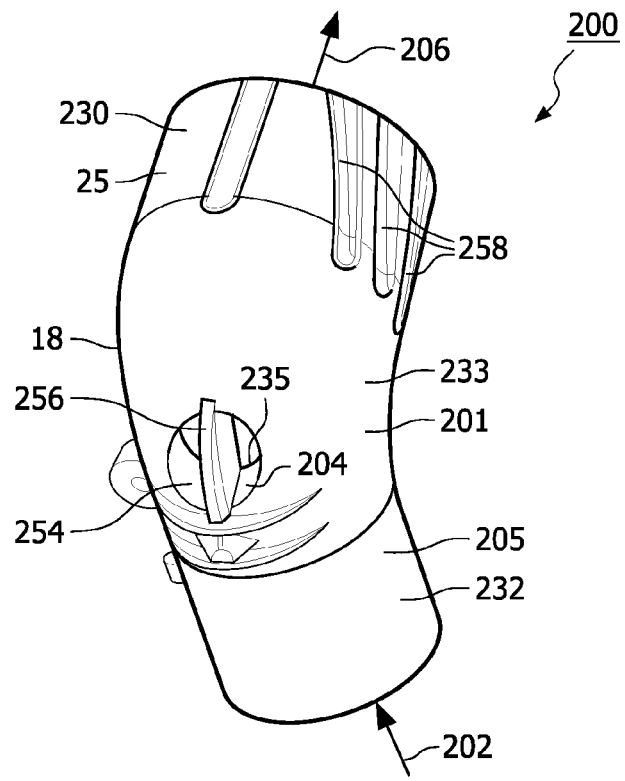
FIG. 4 is an upper right perspective view of an air entrainment valve with exhaust ports assembly in accordance with an embodiment of the present invention.

FIG. 4 shows a conduit 18 in accordance with one embodiment. In this embodiment, the conduit 18 is an entrainment valve assembly 200. The entrainment valve assembly 200 comprises a generally an elbow shaped tubular member 201 formed from a rigid plastic material, such as polycarbonate or other plastic material as would be appreciated by one skilled in the art. In one embodiment, the tubular member 201 is formed from a clear, colorless, plastic material. Tubular member 201 includes a primary inlet 202, a secondary inlet 204 and an outlet 206.

Tubular member 201 includes a first connector portion 230 and a second connector portion 232. The first connector portion 230 and the second connector portion 232 are generally cylindrical in shape and are generally disposed perpendicular to each other. The first connector portion 230 and second connector portion 232 is joined by a bent tubular region 233.

The first connector portion 230 has aforementioned generally cylindrical outer surface 25 for connection with the breathing circuit interface 16, while the second connector portion 232 also has a cylindrical outer surface 205 for frictionally mating with the inner surfaces of tubing.

The second connector portion 232 is connected to the breathing circuit tubing (not shown) and receives pressurized gas from a source of pressurized gas (e.g., air from a CPAP machine, a blower, a ventilator or other ventilation device).

The secondary inlet 204 of the entrainment valve assembly 200 comprises an opening 254 located towards the bent tubular region 233. The opening 254 is divided into two equal, generally semi-cylindrical segments by a planar wall 256. The planar wall 256 of the entrainment valve assembly 200 extends through the cylindrical opening 254. The opening 254 allows the user 27 to breath in from and out to atmosphere in the absence of pressurized gas flow being provided into inlet 202. The entrainment valve assembly 200, at cylindrical surface 25, further includes a plurality of exhalation grooves 258. The grooves 258 are located at an interface where the entrainment valve assembly 200 connects with the breathing circuit interface 16 as will be more fully appreciated from FIG. 19. The plurality of the exhalation grooves 258 are circumferentially spaced on surface 25 and placed symmetrically on either side of the first connector portion 230. Other embodiments are contemplated in which the exhalation grooves 258 are located anywhere on the outer surface of the first connector portion 230, where it interfaces with breathing circuit interface 16.

As clearly shown in FIG. 3, the four exhalation grooves 258 on each side of the entrainment valve tubular member 201 are placed at an angle with respect to the horizontal axis on the surface 25 of the entrainment valve 200. Specifically, when the tubular member 201 is connected to the rigid portion 21 such that the second connector portion 232 of the tubular member 201 points downwards, the four exhalation grooves 258 on one side of the tubular member 201 point upwards at an angle whereas the four exhalation grooves 258 on the other side of the tubular member 201 point downwards at an angle. The angular positioning of the grooves 258 allows the exhaled gas to exit the mask in a swirling motion. In addition, the angled groove 258 aid in providing a releasable friction fit between the cylindrical mating surface 25 of the entrainment valve assembly 200 and the cylindrical inner surface 23 of the breathing circuit interface 16.

The exhalation grooves 258 are sufficiently long so that, when the entrainment valve assembly 200 is pushed as far as it can go into the breathing circuit interface 16, the grooves 258 still extend outwardly from the breathing circuit interface 16 and provide a path for allowing the exhaled gas to exit through the grooves 258. In addition, for any extent of friction fitting engagement between the surfaces 23, 25, the cross-sectional area of the gap or space provided by the grooves 258 will be constant, so that the expired gas flow path to the exterior of the mask 258 provides constant resistance, irrespective of whether the entrainment valve assembly 200 is fully inserted or somewhat less than fully inserted into the breathing circuit interface 16.

Figure 5:
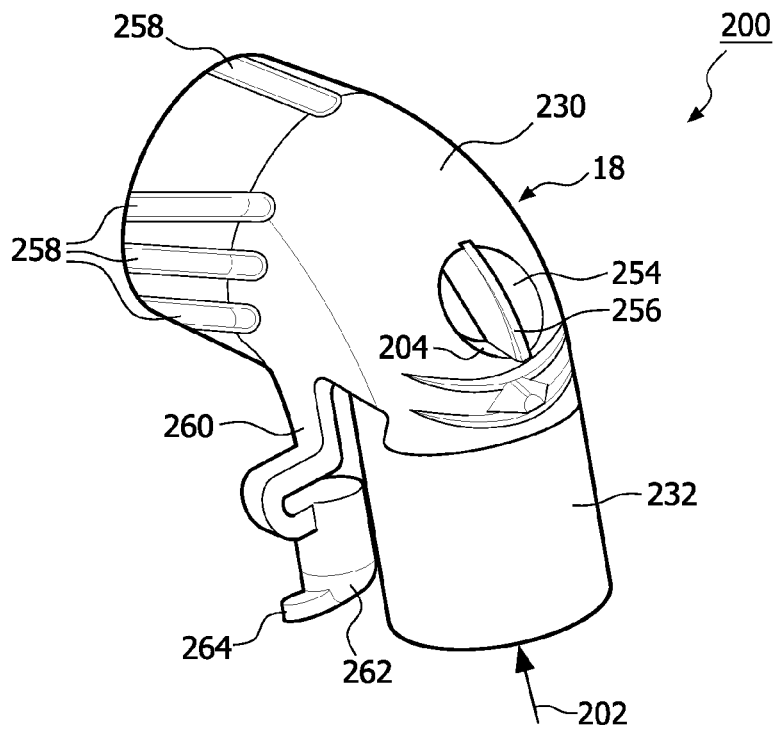
FIG. 5 is a left side perspective view of the air entrainment valve with exhaust ports assembly in accordance with an embodiment of the present invention.

Referring to FIG. 5, the entrainment valve assembly 200 includes a pressure port 260. The pressure port 260 extends from the bent tubular region 233 of the entrainment valve assembly 200 and is generally parallel to the second connector portion 232 of the entrainment valve assembly 200. A removable cap 262 is used to close the pressure port 260. The cap 262 includes gripping tab 264 to aid in removal of the cap 262 from the pressure port 260. A sampling tube (not shown) may be disposed in fluid communication with the gas within tubular body 201 through the pressure port 260. A transducer (not shown) can be secured to the sampling tube, and a processor communicates with the transducer. The processor calculates at least one respiratory parameter using the signal from the transducer. This is generally used to measure pressure by the ventilator as control feedback to the ventilator.

Figure 6:
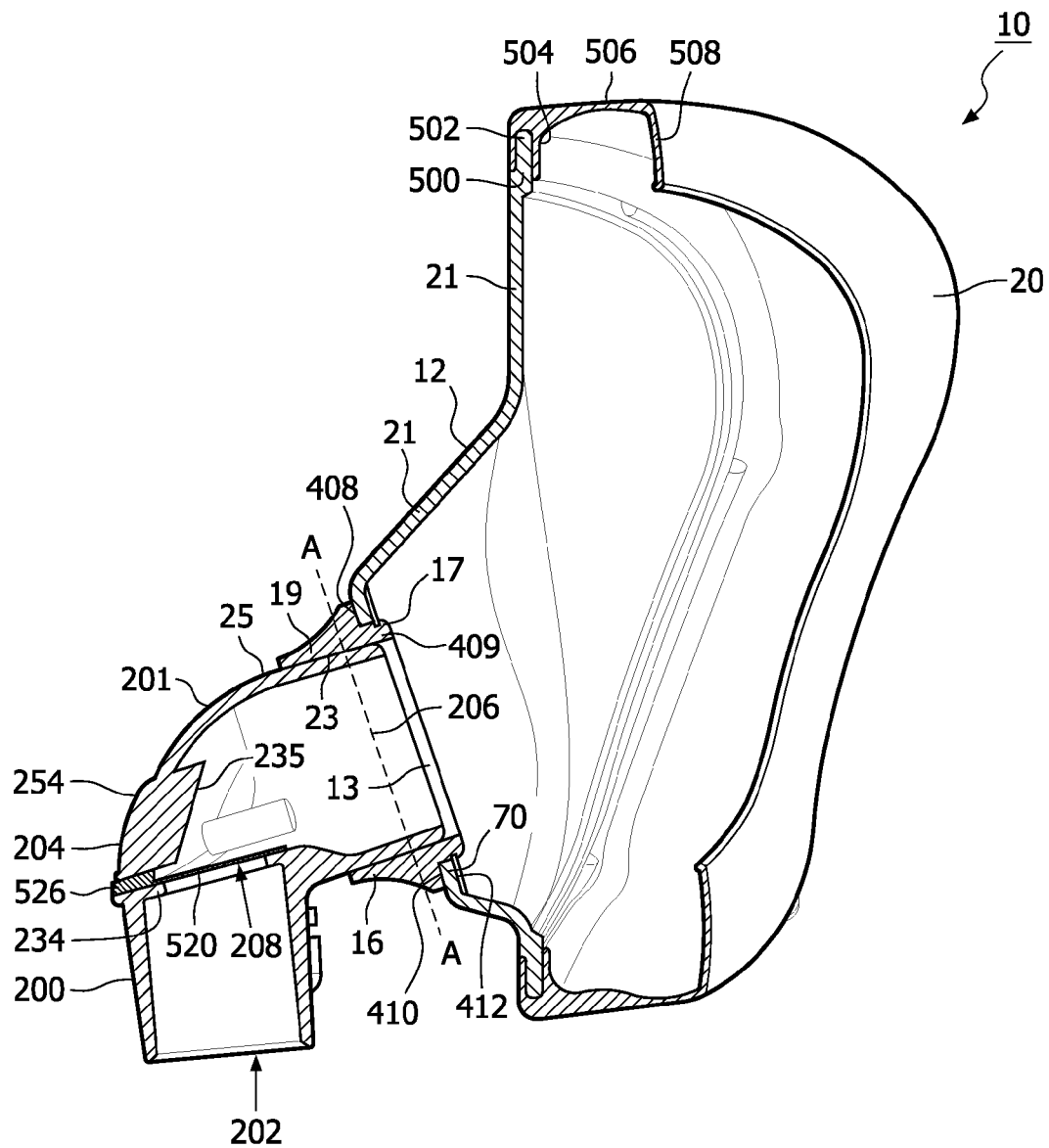
FIG. 6 is a cross-sectional view of the mask assembly in accordance with an embodiment of the present invention.
Figure 7:
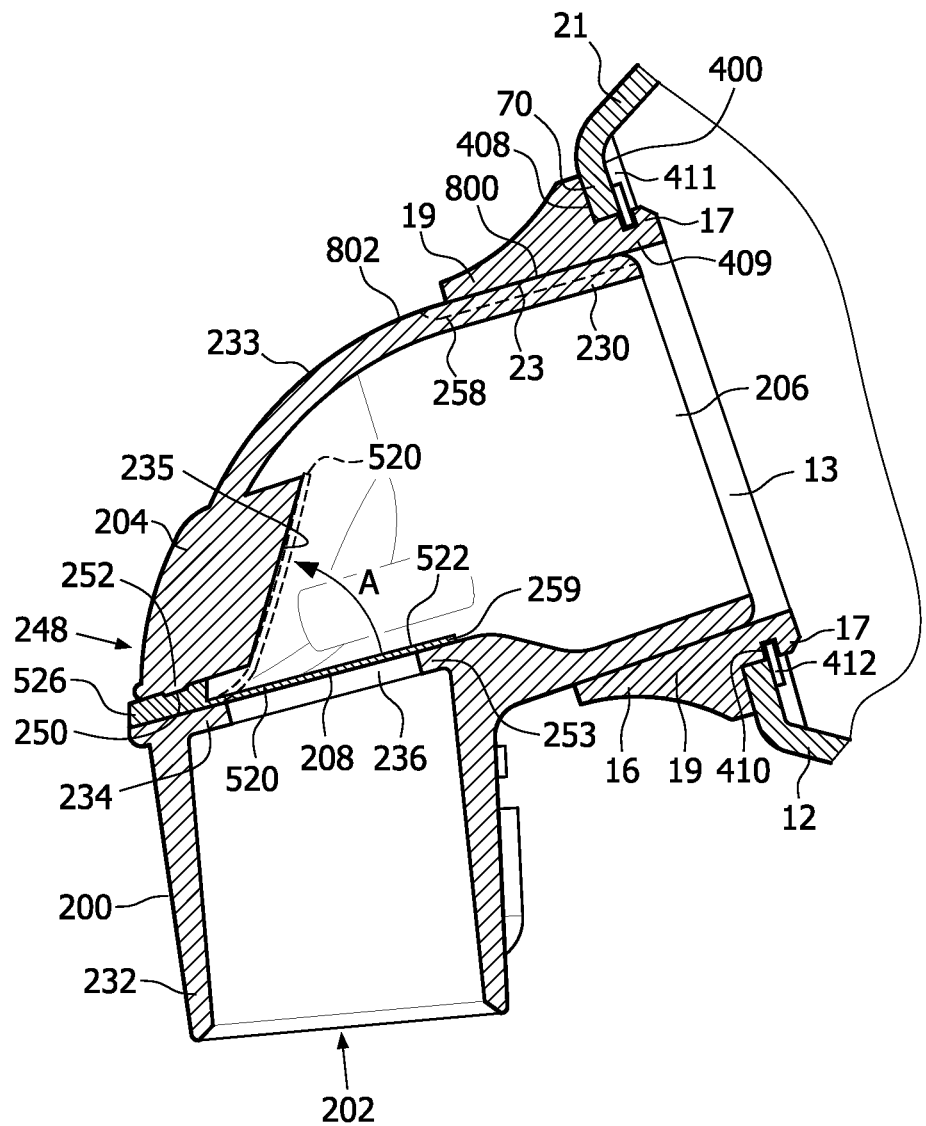
FIG. 7 is a cross-sectional view of the entrainment valve assembly in accordance with an embodiment of the present invention.

As shown in FIGS. 6 and 7, the breathing circuit interface 16 includes the aforementioned first portion 17 and second portion 19. The first portion 17 is generally circular in shape and includes an annular flat wall 408 that engages a radially inwardly extending flange portion 70 in slidable surface relationship. The flange portion 70 surrounds opening 13 in the rigid portion 21 of the mask body 12 (see FIG. 3). The first portion 17 of the breathing circuit interface 16 further includes generally cylindrical protruding portion 409 that extends outwardly from a radially innermost portion of annular surface 408. The cylindrical protruding portion 409 extends into the opening 13 in the rigid portion 21 of the mask body 12. The cylindrical protruding portion 409 has a groove 410 located in the outer cylindrical surface thereof (see FIG. 7). The groove 410 accommodates a connecting washer or a bearing 412. The washer 412 in one embodiment is a split ring washer structure that has an outer periphery thereof that bears against the inner surface of the flange 70, and its inner periphery received groove 410 so as to rotatably connect the breathing circuit interface 16 with the mask body 12. Thus, the breathing circuit interface 16 is rotatably connected with the rigid portion 21 of the mask body 12. Slight friction at the rotatable interface may, in one embodiment, provide at least resistance to rotation, so that the rotational position of the breathing circuit interface 16 can be manually set as desired, and it will retain that position so that the leg or the second connector portion 232 of the conduit 18 that connects with tubing can be positioned in a desired direction that is generally retained unless intentionally altered. In another embodiment, the friction at the point of rotation can be minimal, to allow free rotation of the breathing circuit interface 16.

In another embodiment, the connection between the breathing circuit interface 16 and the rigid portion 21 of the mask body 12 may be achieved by using a ball bearing arrangement or any other type bearing arrangement that allows a rotating motion of the breathing circuit interface 16 with respect to the mask body 12.

As discussed above, the inner surface 23 of the breathing circuit interface 16 is shaped and configured to engage detachably with an outer surface 25 of the entrainment valve assembly 200 by a friction-fit. In addition to allowing friction fit with the entrainment valve assembly 200, the inner surface 23 of the breathing circuit interface 16 allows the entrainment valve assembly 200 to be removed and interchangeably friction fitted with different, other types of the conduits 18 through a similar friction fit, as will be described in more detail later. The diameter of the first connector portion 230 is larger than the diameter of the second connector portion 232 of the entrainment valve assembly 200 to prevent the wrong end of the valve assembly 200 from being connected with interface 16.

Figure 8:
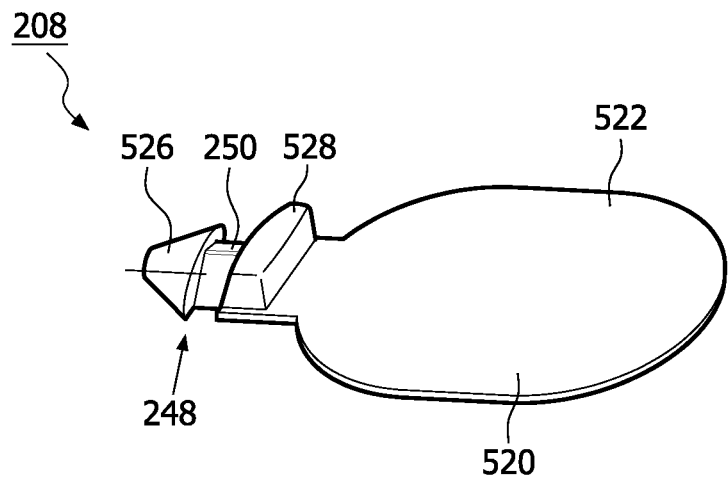
FIG. 8 is a perspective view of a valve element in accordance with an embodiment of the present invention.
Figure 9:
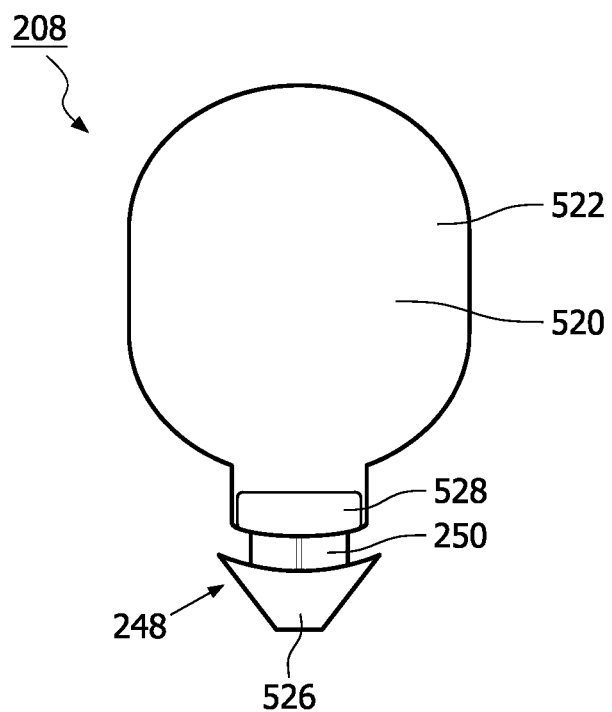
FIG. 9 is a top perspective view of a valve element in accordance with an embodiment of the present invention.

The entrainment valve assembly 200 includes a valve member 208. The valve member 208 is connected to the tubular member 201 at connection region 248 thereof by means of a recess 250 and a barb 526 and a stop member 528 provided in the valve member 208 (see FIGS. 8 and 9). A rib 252 (see FIG. 7), located on the lower portion of the bent tubular region 233 of the entrainment valve assembly 200, has an outer surface thereof that is received in recess 250 so as to clamp the connecting region 248 against a portion 234 of an annular flange 253.

The valve member 208 has a sealing portion 520, having a relatively thin, flat, oval configuration. The sealing portion 520 is made of a flexible material and thus capable of bending upwardly (as shown in the dashed lines in FIG. 7) in response to pressurized gas being forced into the primary inlet 202. The upward bending continues until an upper surface 522 of the sealing portion 520 engages an annular lip 235 at the end of a cylindrical wall 254 protruding into the tubular body 201 and defining the secondary inlet 204. The direction of travel of the sealing portion 520 from its rest position to the upper bent portion is shown by arrow A in FIG. 7. In this upper bent portion, the sealing engagement of the upper surface 522 of the valve member 208 with annular lip 235 causes the secondary inlet 204 to be sealed so that pressurized gas provided into the primary inlet 202 does not escape through the secondary inlet 204.

It should be noted that where gas is not being provided to the patient through the primary inlet 202 (e.g., the blower connected with the primary inlet 202 is not operating), the secondary inlet 204 may serve as both an inlet passage of atmospheric air provided to the patient during inhalation and an outlet passage for exhalation. In this instance, the sealing portion 520 may remain at its at rest position, wherein it forms a seal with an upper surface 259 of the annular flange 253, as shown in FIG. 7.

The valve member 208 can be made from rubber, latex, silicone, or any other elastomeric material as would be appreciated by one skilled in the art.

Figure 19:
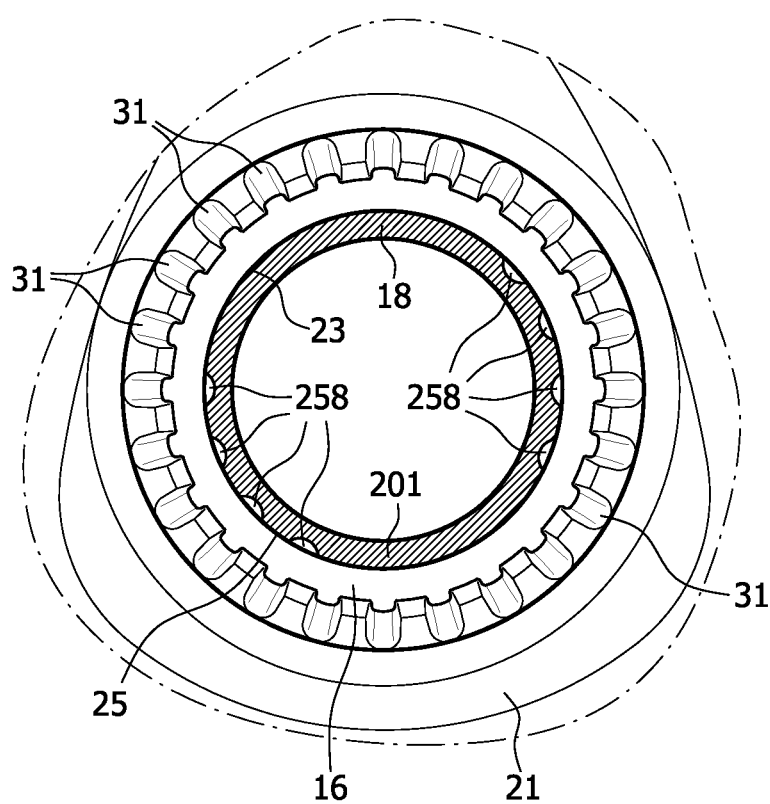
FIG. 19 is a cross-sectional view taken through the line A-A in FIG. 6 and showing the passage of the exhalation grooves through the breathing circuit interface in accordance with an embodiment of the present invention.
Figure 20:
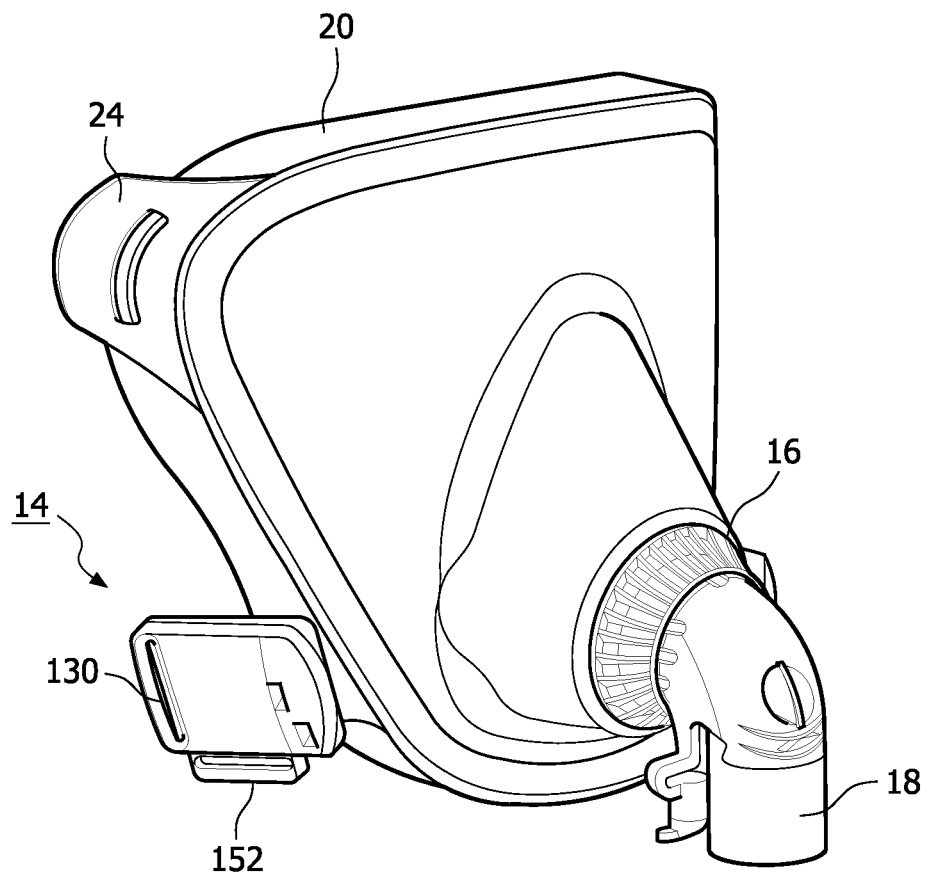
FIG. 20 is a front perspective view of an alternative embodiment of the mask assembly.
Figure 21:
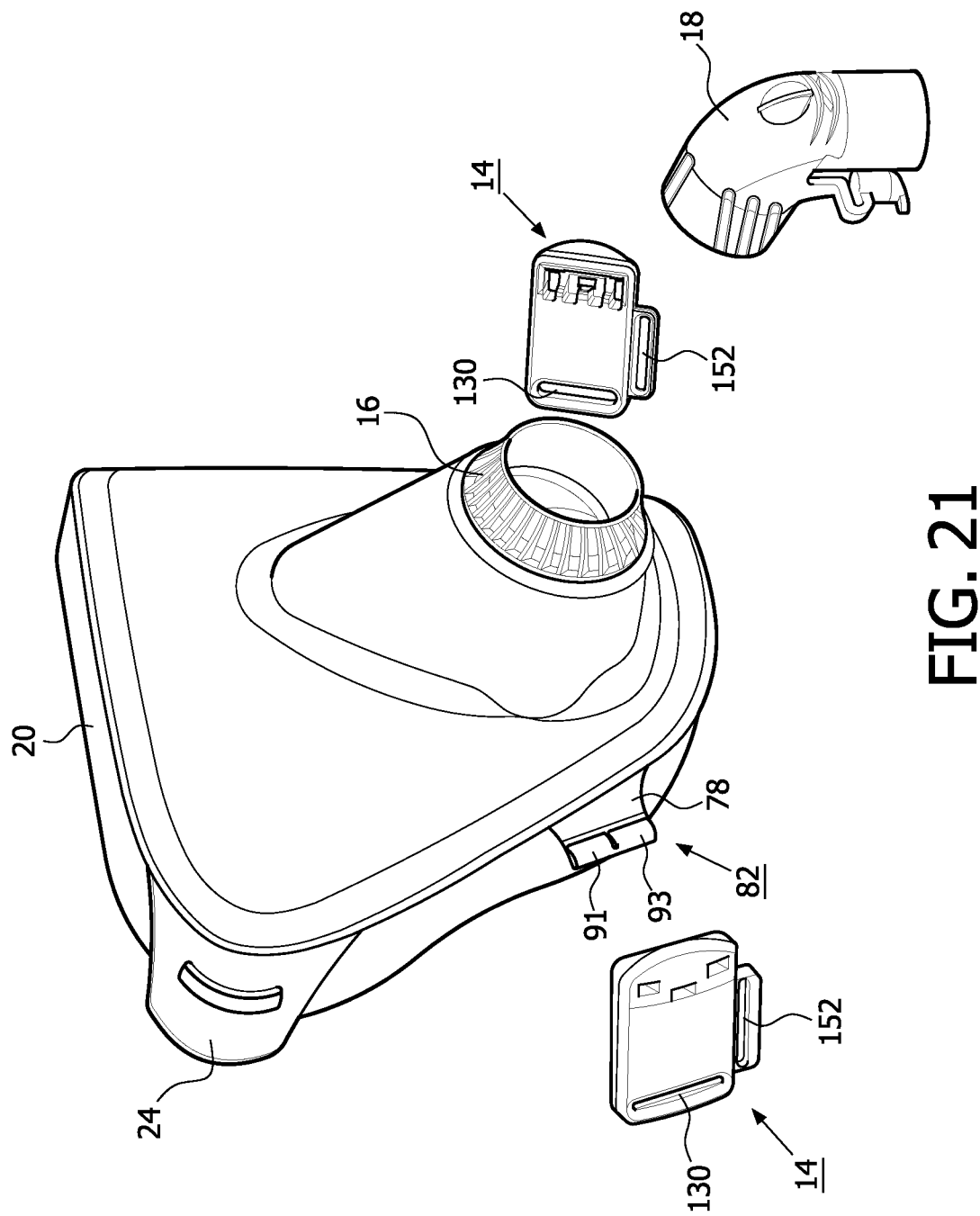
FIG. 21 is an exploded front perspective of the mask assembly in accordance with an embodiment of the present invention.

As can be appreciated most readily from FIG. 4 and FIG. 19 (which is a cross-sectional view taken through A-A in FIG. 6), the exhalation grooves 258 form a passage between the exterior surface 25 of the tubular portion 201 and the interior cylindrical surface 23 of the breathing circuit interface 16. In one embodiment, the exhalation grooves 258 are provided on opposite lateral sides of the exterior surface 25 of the tubular portion 201. In another embodiment, the exhalation grooves may be provided on the inner surface 23 of the breathing circuit interface 16 rather than on body 201. In addition, as shown as dashed lines in FIG. 7, in another embodiment they may alternatively, or also, be located at the top portion of the exterior surface 25 of the body 201. When the user inhales, a very small fraction of gas may be drawn from atmosphere through the exhalation grooves 258. However, by and large, the pressurized gas forced into the primary inlet 202 will create higher pressure within the body 201 than the atmospheric pressure, so that air is mostly forced outwardly through the exhalation passages 258 (rather than inwardly), even during inhalation. Moreover, as the user exhales, the exhaled gas impacts the centrally incoming airflow through the body 201 and is thus forced to mushroom radially outwardly resulting in a circular flow pattern that effectively flushes the exhaled gas, and is thus generally directed toward and through the peripheral exhalation grooves 258 to atmosphere.

As best seen in FIG. 6, the flexible peripheral seal portion 20 may have a generally rectangular channel shaped cross-sectional configuration with three sides 504, 506 and 508. The flexible peripheral seal structure 20 may be attached to the mask body 12 at side 504. An edge 500 of the rigid portion 21 of the mask body 12 engages with an opening 502 located in the side 504 of the flexible peripheral seal structure 20, such that a layered connection is formed. The parts are then adhered in place, through an adhesive connection, an ultrasonic weld connection, a riveted or a pinned connection or any other type of connection as would be appreciated by one skilled in the art. Other embodiments are contemplated in which there is no overlap, such as by attaching the rigid portion 21 and flexible peripheral seal structure 20 with their edges end to end (e.g., by an adhesive connection). The side 506 is located between side 504 and side 508, providing a gap between sides 504 and 508. This gap may provide flexibility to the flexible peripheral seal portion 20, as it conforms to the face of the user 27. The corners of the flexible peripheral seal portion 20 may be generally rounded. The length of the sides 508 and 506 may vary along the periphery of the seal structure 20 so as to provide a conforming sealing engagement of the mask body 12 with the face of the patient 27.

Figure 10:
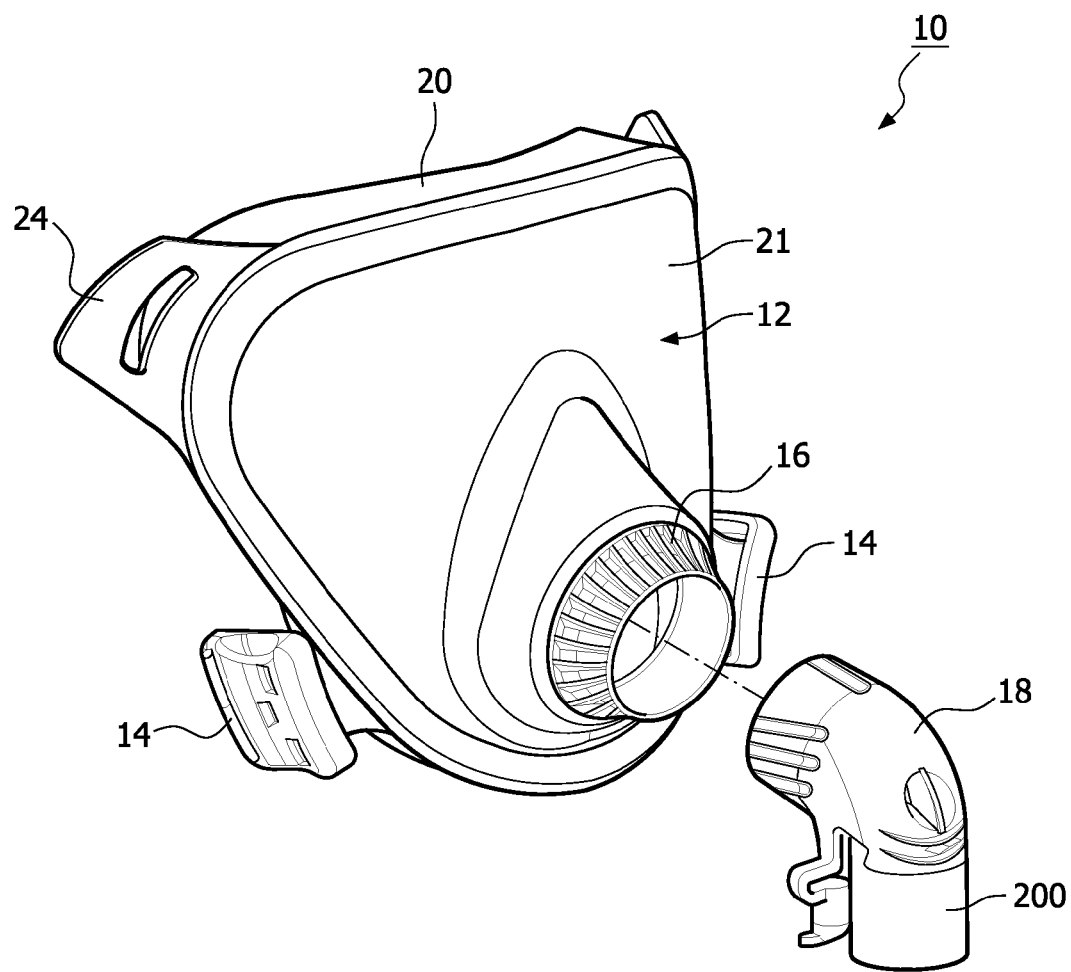
FIG. 10 is a perspective view of the mask body and the entrainment valve assembly in accordance with an embodiment of the present invention.
Figure 11:
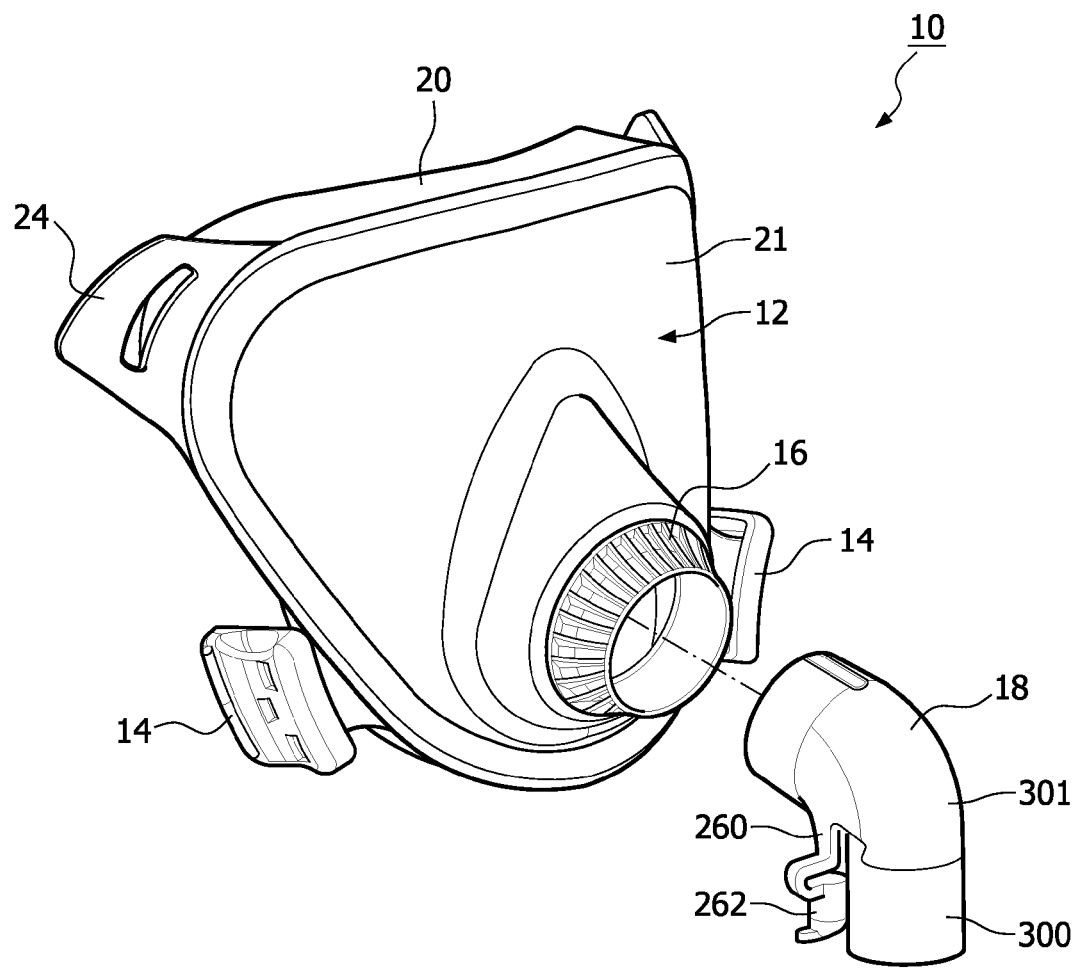
FIG. 11 is a perspective view of the mask body and a standard elbow before the assembly in accordance with an embodiment of the present invention.
Figure 12:
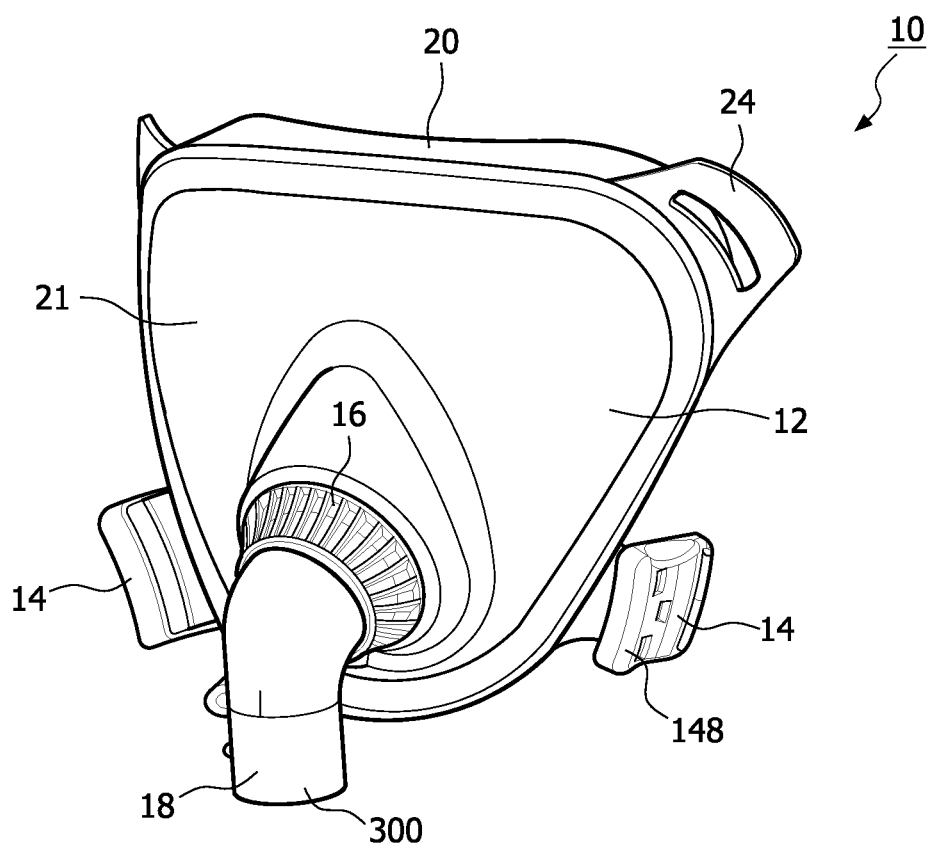
FIG. 12 is a perspective view of the mask body and the standard elbow after the assembly in accordance with an embodiment of the present invention.

FIGS. 10-12 show the replaceable and interchangeable concept of the conduit 18 with respect to the breathing circuit interface 16. Specifically, in FIGS. 10-12, the entrainment valve assembly 200 is shown being replaced by a standard elbow 300, both of which can be used as examples for the conduit 18. However, as discussed later, other elbow configurations may also be friction fitted with the breathing circuit interface 16.

FIG. 10 shows the entrainment valve assembly 200 having been removed from the mask assembly 10. This can be done by simply pulling the entrainment valve assembly 200 away from the mask assembly 10 to release friction fit as discussed earlier. FIGS. 11 and 12 show the mask assembly 10 being connected with the standard elbow 300 by a similar friction fit. The standard elbow 300 has no internal valve and no exterior exhalation grooves. The standard elbow 300 provides a tubular, elbow shaped body 301 that is otherwise similar to tubular body 201 for providing a connection between the breathing circuit interface 16 and the tubing that will provide breathing gas to the mask assembly 10. The standard elbow 300 may optionally be provided with the pressure port 260 and pressure cap 262 as discussed with respect to the entrainment valve assembly 200. In one embodiment, body 301 is formed from a clear (transparent), but colored (e.g., blue) plastic material.

The removable and replaceable conduits 18 enable the mask assembly 10 to be functional for different uses, simply by employing the conduit 18 of choice.

Though FIGS. 10-12 show the mask assembly 10 that is adapted to accommodate the entrainment valve assembly 200 and standard elbow 300 interchangeably, listed below are some non-limiting examples of other types of conduits 18 that can be used interchangeably with the mask assembly 10 described above:

Conduit with a bronchoscope port to permit the care giver to perform a bronchoscopy procedure with mask on Conduit with aerosol generator adapter to deliver medication during NIV Conduit with MDI port to deliver medication using a "Metered Dose Inhaler"

Conduit with port to accommodate a CPAP relief valve

Conduit with C02 sensor capabilities to monitor patient

Conduit with Volumetric C02 sensor capabilities to monitor patient VC02

Conduit that entrains Heliox or other specialty gases

Conduit that adds moisture to inhaled gas

Conduit that includes an HME [Heat moisture exchanger]

Conduit that incorporates "nano" sensors for a variety of clinical monitoring capabilities Conduit with Filtered Exhalation [useful in pandemic situations like SARS]

Conduit that enhances the patients ability to "Speak with Mask On"

Conduit that accommodates a NG feeding tube

Conduit that reduces/control C02 re-breathing

Conduit that aids in secretion clearance
Conduit with Standard Elbow
Conduit that can be used on a wide range of mask types [Such as Full, Nasal or Total or Helmet]

It should be appreciated, that the above listed conduit configurations provide non-limiting examples of different types, configurations and/or constructions of conduits that can be provided. It should be appreciated that, while these conduits may all be provided with an elbow shaped tubular body; other tubular shapes (such as a straight tubular configuration) may alternatively be provided.

Other embodiments are contemplated in which the connection between the conduit 18 and the breathing circuit interface 16 is not a friction fit, but may be achieved by virtue of other types of connections such as a quarter-turn type connection, a snap fit, or any other locking mechanism that provides a detachable connection between the conduit 18 and the breathing circuit interface 16.

In yet another embodiment, the first connector portion 230 of the conduit 18 may itself be provided with a swivel coupling, similar to the breathing circuit interface 16, rather than such structure being provided as part of the mask. In that case, the swivel coupling of the elbow can be connected directly to a non-swiveled portion (e.g., an outwardly projecting cylindrical configuration) surrounding the opening 13 in the rigid portion 21 of the mask body 12.

In yet another embodiment, no swivel coupling is provided. Rather, a direct connection between the tubular body (e.g., 201 or 301) is provided with a correspondingly shaped portion of the rigid portion 21 of the mask. In this embodiment, some rotation of the conduits 18 may nevertheless be accommodated via direct sliding friction at the friction fit connection between rigid portion 21 and the tubular body. However, it is further contemplated that other, non-rotational connections may also be provided and will still enable the modularity of design contemplated herein.

In one aspect of the invention, a mask assembly kit is provided. The kit assembly includes the mask body 12, with or without the rotatable interface 16, and at least two conduits 18 of different types to enable the mask body 12 to provide different functionality simply by changing conduit types. For example, the standard elbow 300 (valveless) can be provided as one conduit, and the entrainment valve assembly 200 can be provided as another conduit. More than two conduits may be provided, and more than one mask may be provided, although each of the masks will have a common configuration, while the conduits will have at least two different configurations that fit the mask body.

Figure 13:
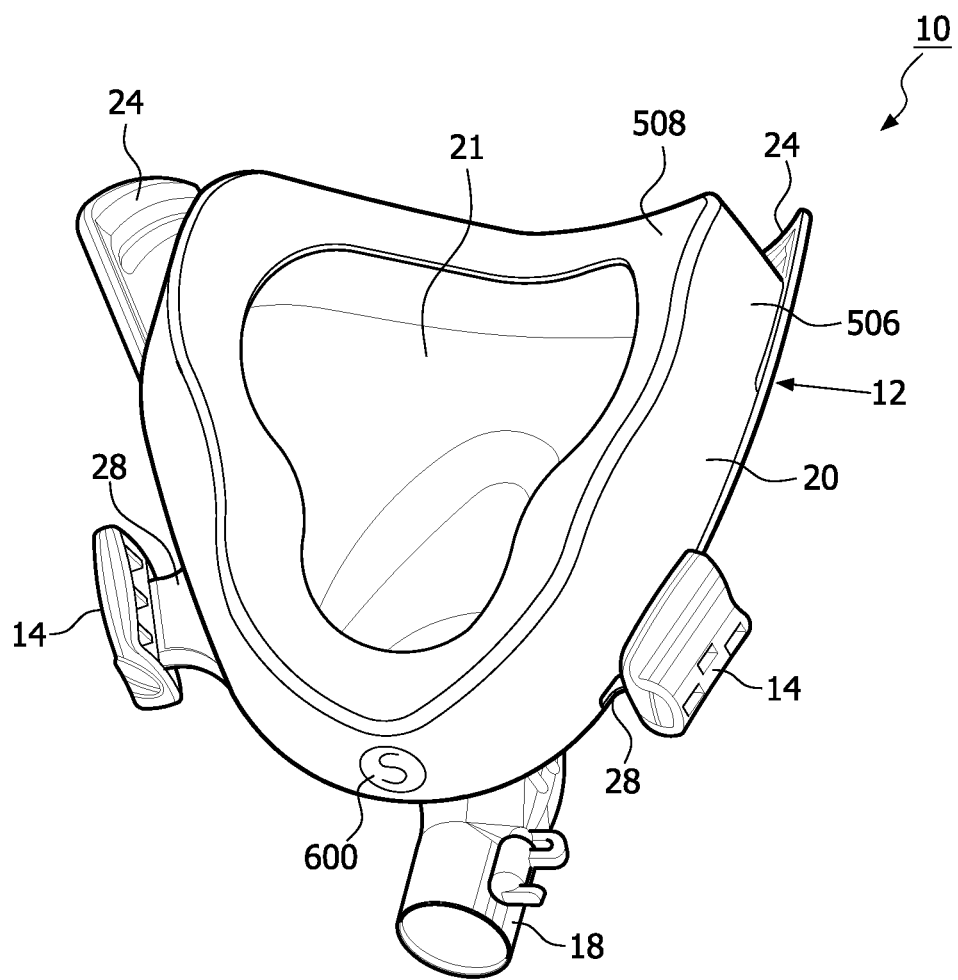
FIG. 13 is a rear perspective view of the mask assembly in accordance with an embodiment of the present invention.
Figure 14:
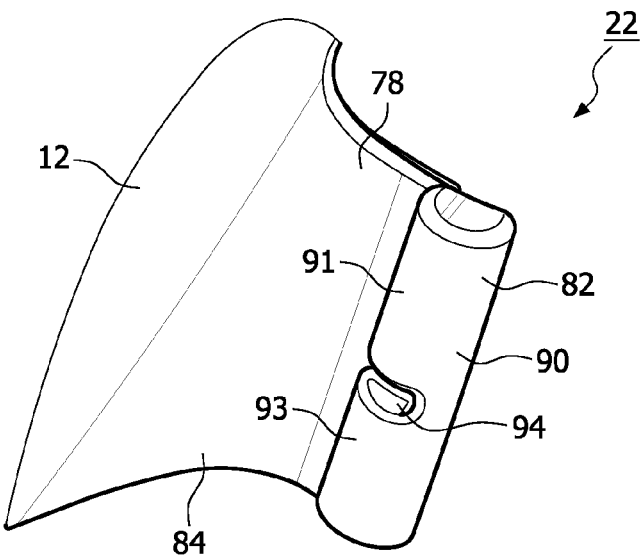
FIG. 14 is a front perspective view of a mask headgear attachment post in accordance with an embodiment of the present invention.
Figure 15:
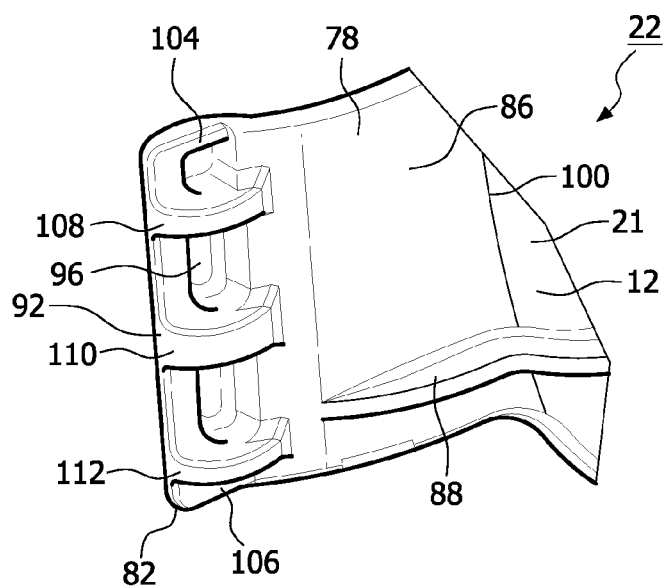
FIG. 15 is a rear perspective view of the mask headgear attachment post in accordance with an embodiment of the present invention.
Figure 16:
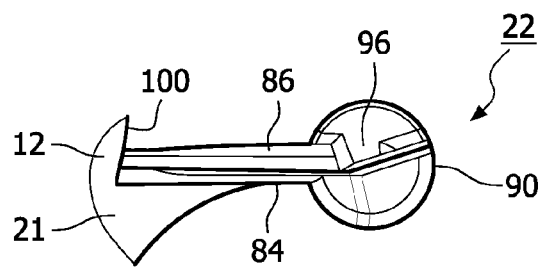
FIG. 16 is a side perspective view of the mask headgear attachment post in accordance with an embodiment of the present invention.

FIG. 13 shows a rear perspective view of the mask assembly 10. The flexible seal structure 20 can be clearly seen here. Also shown are the headgear strap retaining tabs 24 and portions of headgear attachment members 22, which are partially obstructed by the headgear attachment clips 14. FIGS. 14-16 show the headgear attachment members 22 more clearly. The headgear attachment members 22 are integrally formed with the rigid portion 21 and extend outwardly therefrom, beyond the flexible peripheral seal structure 20. Specifically, the headgear attachment members 22 each have a generally flat web portion 78 integrally connected with the rigid portion 21 of the mask body 12, and a connecting post or barrel 82 disposed at the outer end of the web portion 78. The web portion 78 gradually tapers from the mask body 12 to the barrel 82. The headgear attachment members 22 each include a front surface 84 and a rear surface 86. A reinforcement rib 88, which extends along the web 78 from the mask body 12 to the barrel 82, is provided on the rear surface 86 on each of the webs 78. Each barrel or post 82 includes a front face 90 and a rear face 92. The front face 90 of the barrel 82 is generally semi-cylindrical in shape with a groove 94 located centrally thereof, as best seen in FIG. 14. The front face 90 has an upper semi-cylindrical surface portion 91 and a lower semi-cylindrical surface portion 93 on opposite sides of groove 94. The rear face 92 of the barrel 82 includes a channel 96 located between opposite ends 104 and 106 of the barrel 82. The channel 96 is divided into four segments by three generally semi-circular projections 108, 110 and 112 (top projection 108, middle projection 110, and bottom projection 112). The thickness of the central circular projection 110 is greater than the thickness of the circular projections 108 and 112.

Figure 17:
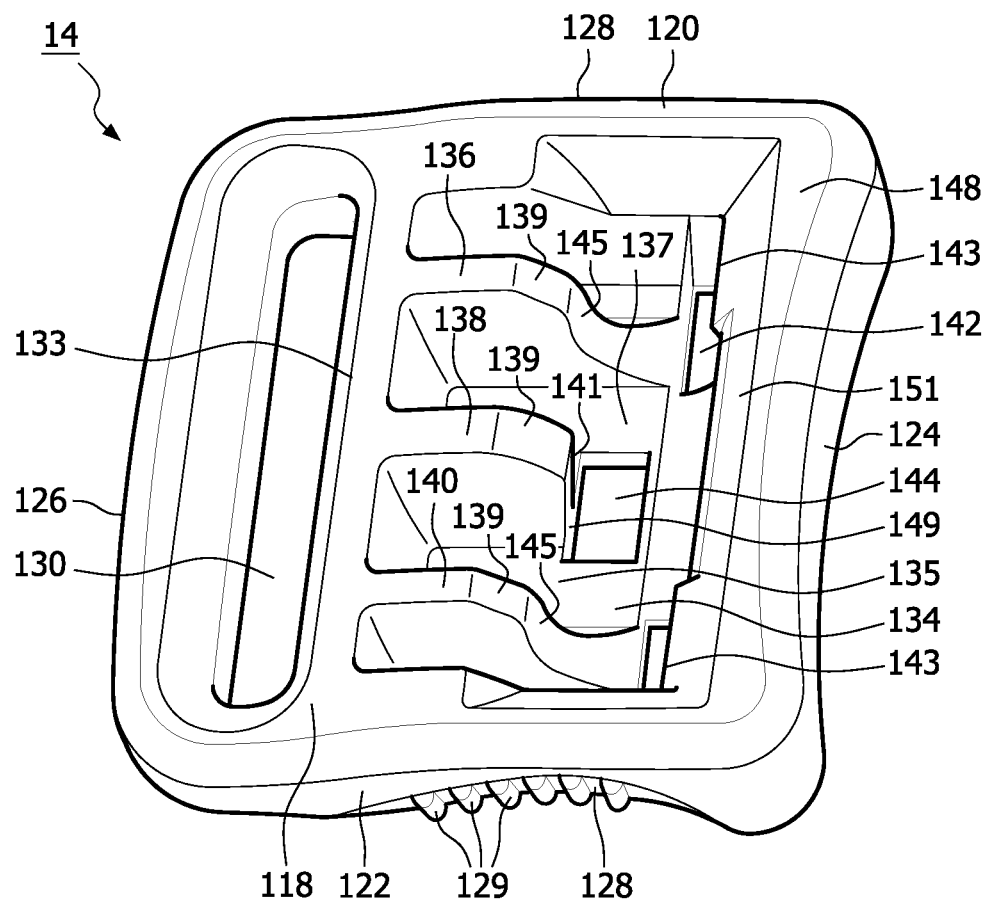
FIG. 17 is a rear perspective view of a mask headgear attachment clip in accordance with an embodiment of the present invention.
Figure 18:
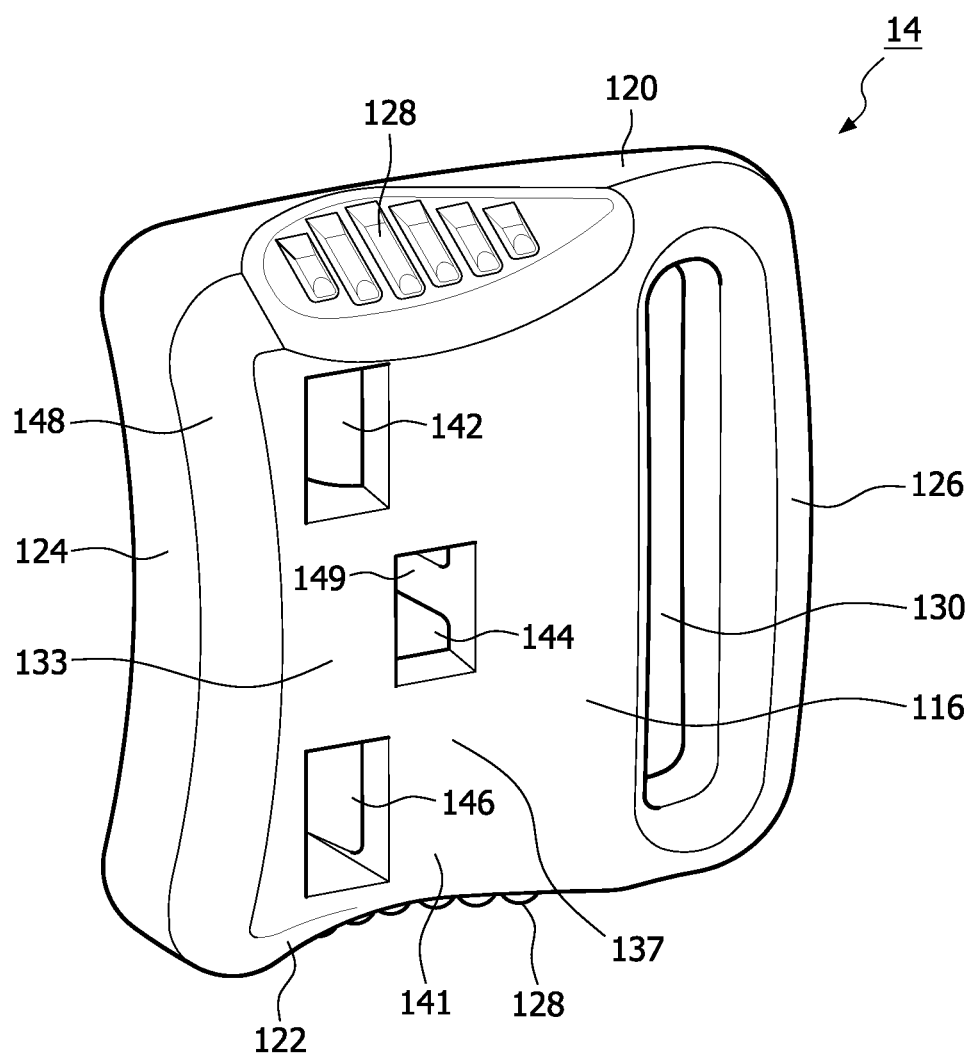
FIG. 18 is a front perspective view of the mask headgear attachment clip in accordance with an embodiment of the present invention.

FIGS. 17 and 18 show one of the headgear attachment clips 14. The headgear attachment clips 14 each include a front face 116, a rear face 118, a top face 120, a bottom face 122, a first side face 124 and a second side face 126. When the headgear attachment clip 14 is assembled with the mask body 12, the top face 120 faces upwards towards the headgear strap retaining tabs 24 of the mask body 12, the bottom face 122 faces away from the headgear strap retaining tabs 24 of the mask body 12, the first side face 124 faces the mask body 12, and the second side face 126 faces away from the mask body 12. Finger indentations 128 having gripping ribs 129 are located on the top face 120 and the bottom face 122 of the headgear attachment clips 14. The gripping ribs 129 provide a region for the patient 27 or care giver to grip the headgear attachment clips 14 while securing or removing the headgear assembly 11 with the mask body 12. The headgear attachment clips 14 include an elongated opening 130 that receives the straps 40 of the headgear assembly 11.

As shown in FIG. 17, the rear face 118 of the headgear attachment clips 14 includes a cavity 134, which is generally rectangular in shape and includes three cam fingers 136, 138 and 140 that extend from a wall 133 defining one side of the elongated opening 130. The cam fingers 136, 138 and 140 extend about half way through the cavity 134. The thickness of the central cam finger 138 is greater than the thickness of the upper and lower cam fingers 136 and 140 respectively. The cam fingers 136, 138 and 140 are generally rectangular in shape and connected along one side to wall 133 and on the bottom to a bottom wall 137 of the cavity 134. Each of the cam fingers 136, 138 and 140 has a chamfered edge located on the top corners 139 that are located away from the side wall 133. The edges 145 of the cam fingers 136 and 140 that extend downwardly from the corners 139 are sloped at a positive angle so that they extend away from wall 133 as they extend downwardly to join bottom wall 137. In contrast, the chamfered corner 139 on the central cam finger 138 terminates at a hard corner 141 that protrudes slightly beyond the edges 145 of cam fingers 136 and 140, and then extends at a negative angle to form an undercut, such that its forward edge 149 extends slightly in a direction towards wall 133 as it extends towards bottom wall 137. The hard corner 141 provides a primary point of camming contact with the barrel 82 (and in particular, central projection 110 thereof) to lock and unlock (or connect and disconnect) the barrel 82 to the headgear attachment clip 14 as will be described. The cavity 134 includes an elongated channel 135 that does not contain the cam fingers 136, 138 and 140. An outer wall 148 of the headgear attachment clip 14 defines one end of the cavity 134, opposite the wall 133. The top portion of wall 148 includes a chamfered top portion 151, and also includes a pair of overhangs 143. The overhangs 143 serve a similar function to the hard corner 141, but engage with semi-cylindrical surfaces 91 and 93 respectively (see FIG. 14), as will be described.

As shown in FIG. 18, the front face 116 of the headgear attachment clips 14 includes three rectangular openings 142, 144 and 146 that are located in the wall 137. The three rectangular openings 142, 144 and 146 extend into the channel 135 of the cavity 134 on the rear face 118 (see FIG. 17). The openings 142 and 146 are disposed closely to outer wall 148, while the opening 144 is offset and disposed at the bottom of sloping surface 149 of cam finger 138.

The headgear attachment clips 14 along with the headgear straps 40 are connected to their respective headgear attachment members 22 by moving the headgear attachment clips 14 toward the barrels 82 so that the channel 135 of the headgear attachment clips 14 are forced onto the barrels 82 of the headgear attachment members 22. Specifically, the cam finger 138 (and specifically, the hard corner 141) of the headgear attachment clips 14 engages with the corresponding semi-circular projection 110 of the barrel 82, and the overhangs 143 of the headgear attachment clips 14 engage with the surfaces 91 and 93 on the opposite side of the barrel 82. A camming motion between the cam finger 138 of the headgear attachment clips 14 and the corresponding circular projection 110 of the barrel 82 of the headgear attachment members 22 causes a bending of the web portions 78, and a slight flexing of the cam finger 138 and/or circular projection 110 to allow the circular projection 110 to move past the hard corner 141 and into the channel 135. Similarly, the flexing movement of web 78, together with slight flexing of the overhangs 143 and/or surfaces 91 and 93 enable the surfaces to be cammed passed the overhangs 143. When the barrel 82 is disposed within channel 135, the overhangs 143 and the hard corner 141 prevents the barrel 82 from escaping the channel 135. The overhangs 143 of the headgear attachment clips 14 engage with the surfaces 91 and 93 on the opposite side of the barrel 82, thus allowing for rotation of the headgear attachment clip 14 during adjustment or to accommodate different head sizes.

In one embodiment, rather than a camming action the headgear attachment clips 14 are pulled off or pushed onto the headgear attachment members 22 by a snapping action over hard corners 141 without camming, and the cam finger 138 of the headgear attachment clips 14 engages with the corresponding semi-circular projection 110 of the barrel 82.

To remove headgear attachment clips 14, the user 27 or caregiver places his fingers on the finger indentations 128 and pulls the headgear attachment clips 14 in a direction away from the flexible peripheral seal structure 20 towards the protrusion 60. The headgear attachment clips 14 rotate about an axis defined by the barrel 82 until the chamfered top portions 151 of the wall 148 engages the front surface 84 of the web 78. Rotational force applied to the headgear attachment clips 14 (e.g., manual force) in a direction forcing surface 151 against surface 84 causes a camming action that creates a flexing of the aforementioned parts and surfaces that lock barrel 82 within channel 135, so as to cam the barrel 82 out of locking engagement within the channel 135. In one embodiment, the headgear attachment clips 14 may be molded from a plastic material, but other materials such as rubber, elastomeric material, or metal are also contemplated.

In another embodiment of the headgear attachment clips 14 as shown in FIGS. 20-23, the headgear attachment clips 14 each include a front face 116, a rear face 118, a top face 120, a bottom face 122, a first side face 124 and a second side face 126. When the headgear attachment clip 14 is assembled with the mask body 12, the top face 120 faces upwards towards the headgear strap retaining tabs 24 of the mask body 12, the bottom face 122 faces away from the headgear strap retaining tabs 24 of the mask body 12, the first side face 124 faces the mask body 12, and the second side face 126 faces away from the mask body 12. The headgear attachment clips 14 include an elongated opening 130 that receives the straps 40 of the headgear assembly 11. In addition, this embodiment includes an auxiliary elongated opening 152. The elongated opening 152 is defined by an inner auxiliary wall 154, an outer auxiliary wall 156, and side auxiliary walls 158. The inner auxiliary wall extends from bottom face 122.

Figure 23:
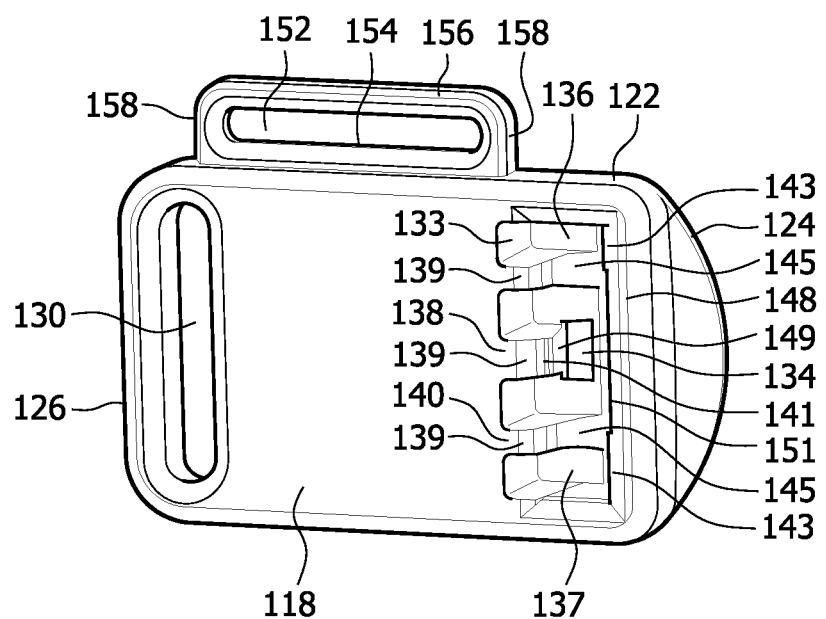
FIG. 23 is a rear perspective of an alternative mask headgear attachment clip in accordance with an embodiment of the present invention.

As shown in FIG. 23, the rear face 118 of the headgear attachment clips 14 includes a cavity 134, which is generally rectangular in shape and includes three cam fingers 136, 138 and 140 that extend from a wall 133 defining one side of the elongated opening 130. The cam fingers 136, 138 and 140 extend about half way through the cavity 134. The thickness of the central cam finger 138 is greater than the thickness of the upper and lower cam fingers 136 and 140 respectively. The cam fingers 136, 138 and 140 are generally rectangular in shape and connected along one side to wall 133 and on the bottom to a bottom wall 137 of the cavity 134. Each of the cam fingers 136, 138 and 140 has a chamfered edge located on the top corners 139 that are located away from the side wall 133. The edges 145 of the cam fingers 136 and 140 that extend downwardly from the corners 139 are sloped at a positive angle so that they extend away from wall 133 as they extend downwardly to join bottom wall 137. In contrast, the chamfered corner 139 on the central cam finger 138 terminates at a hard corner 141 that protrudes slightly beyond the edges 145 of cam fingers 136 and 140 to form an undercut, and then extends at a negative angle, such that its forward edge 149 extends slightly in a direction towards wall 133 as it extends towards bottom wall 137. The hard corner 141 provides a primary point of camming contact with the barrel 82 (and in particular, central projection 110 thereof) to lock and unlock (or connect and disconnect) the barrel 82 to the headgear attachment clip 14 as will be described. The cavity 134 includes an elongated channel 135 that does not contain the cam fingers 136, 138 and 140. An outer wall 148 of the headgear attachment clip 14 defines one end of the cavity 134, opposite the wall 133. The top portion of wall 148 includes a chamfered top portion 151, and also includes a pair of overhangs 143. The overhangs 143 serve a similar function to the hard corner 141, but engage with semi-cylindrical surfaces 91 and 93 respectively (see FIG. 14), as will be described.

Figure 22:
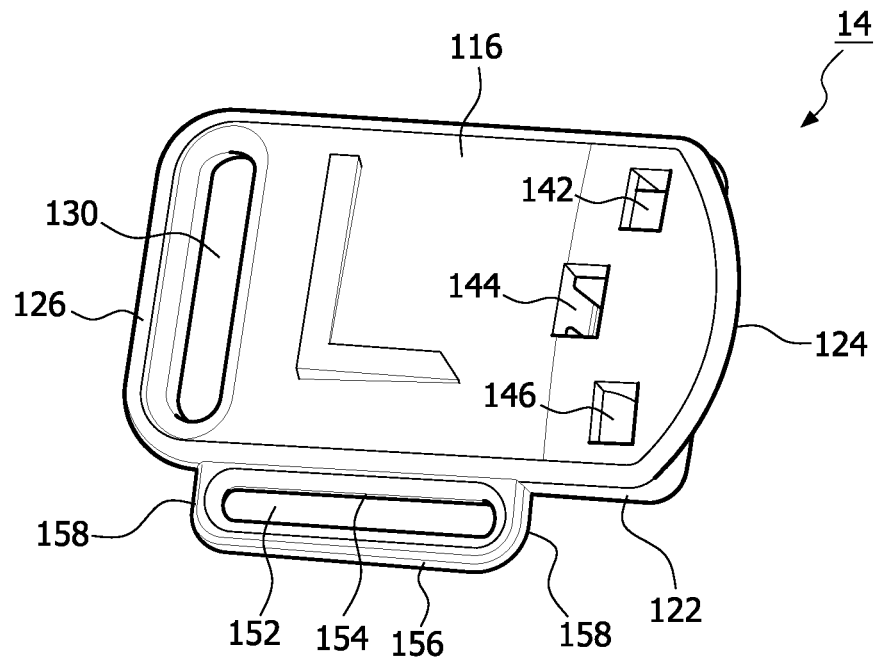
FIG. 22 is a front perspective of an alternative mask headgear attachment clip in accordance with an embodiment of the present invention.

As shown in FIG. 22, the front face 116 of the headgear attachment clips 14 includes three rectangular openings 142, 144 and 146 that are located in the wall 137. The three rectangular openings 142, 144 and 146 extend into the channel 135 of the cavity 134 on the rear face 118 (see FIG. 23). The openings 142 and 146 are disposed closely to outer wall 148, while the opening 144 is offset and disposed at the bottom of sloping surface 149 of cam finger 138.

The headgear attachment clips 14 along with the headgear straps 40 are connected to their respective headgear attachment members 22 by moving the headgear attachment clips 14 toward the barrels 82 so that the channel 135 of the headgear attachment clips 14 are forced onto the barrels 82 of the headgear attachment members 22. Specifically, the cam finger 138 (and specifically, the hard corner 141) of the headgear attachment clips 14 engages with the corresponding semi-circular projection 110 of the barrel 82, and the overhangs 143 of the headgear attachment clips 14 engage with the surfaces 91 and 93 on the opposite side of the barrel 82. A camming motion between the cam finger 138 of the headgear attachment clips 14 and the corresponding circular projection 110 of the barrel 82 of the headgear attachment members 22 causes a bending of the web portions 78, and a slight flexing of the cam finger 138 and/or circular projection 110 to allow the circular projection 110 to move past the hard corner 141 and into the channel 135. Similarly, the flexing movement of web 78, together with slight flexing of the overhangs 143 and/or surfaces 91 and 93 enable the surfaces to be cammed passed the overhangs 143. When the barrel 82 is disposed within channel 135, the overhangs 143 and the hard corner 141 prevents the barrel 82 from escaping the channel 135. The overhangs 143 of the headgear attachment clips 14 engage with the surfaces 91 and 93 on the opposite side of the barrel 82, thus allowing for rotation of the headgear attachment clip 14 during adjustment or to accommodate different head sizes.

In this embodiment, the mask assembly may be provided with an additional strap, not shown, connected between the auxiliary openings 152 and below the chin. This construction provides additional under-the-chin support for the mask 12 to hold it in place rather than permitting it to ride up the patient's face.

The flexible peripheral seal structure 20 of the mask body 12 may be made of a relatively soft and/or flexible material so that the flexible peripheral seal structure 20 conforms to the shape of a patient's face when held against it. The flexible peripheral seal structure 20 may be made of, for example, silicone, an elastomeric material or any other suitable shape conforming material as will be appreciated by one skilled in the art. Different regions of the flexible peripheral seal structure 20 around the perimeter of the mask body 12 may have different cross-sectional configurations. Various other flexible peripheral seal structure 20 configurations will become apparent to those skilled in the art. The flexible peripheral seal structure 20 is generally annular to form a seal around the nose and the mouth and may be generally oblong shaped, pear shaped (as shown in FIG. 13) or any other suitable shape as will be appreciated by one skilled in the art. The rigid portion 21 of the mask body 12, in one embodiment, is made of a relatively more rigid material than the flexible peripheral seal structure 20. For example, mask body 12 may be made from polycarbonate, or other suitable material.

The mask body 12 may be formed by a two-step insert molding process. For example, the rigid portion 21 may be molded first and then inserted into a second mold for the flexible peripheral flexible peripheral seal structure 20, which is injection molded to form around and/or into the rigid portion 21.

Figure 1B:
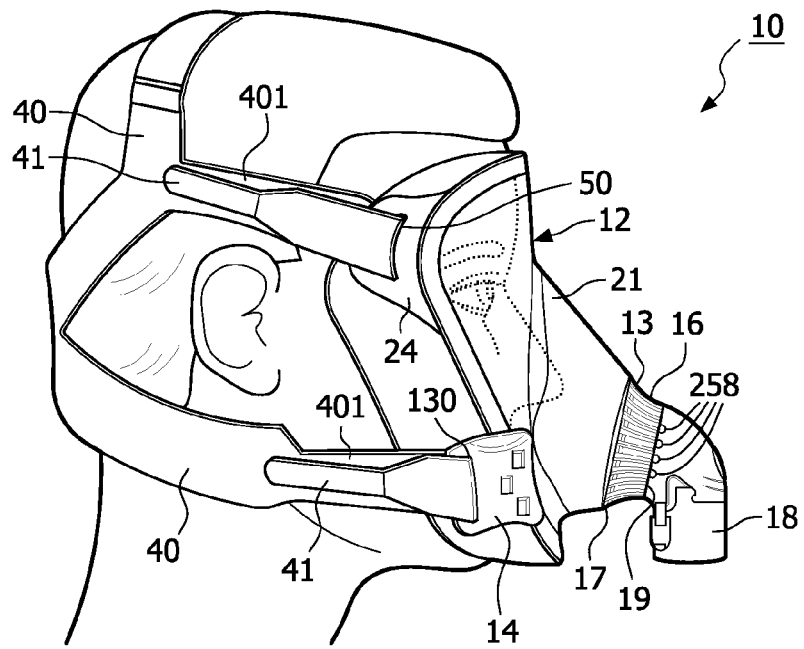
FIG. 1B is a left side perspective view of the mask assembly and patient's face in accordance with an embodiment of the present invention.

In one embodiment, the headgear assembly 11 that is used to mount the mask body 12 to the head of a patient 27 takes the form of straps. However, any structure that secures the mask body 12 to the head of a patient can be used. In the illustrated embodiment as shown in FIGS. 1A and 1B, an end potion 41 of each of the two headgear straps 40 (only one shown in FIG. 1B) is threaded through the elongated opening 50 of the headgear retaining tab 24, and the end portion 41 of the lower headgear straps 40 are threaded through the elongated opening 130 of the headgear attachment clip 14. In one embodiment, the end portion 41 comprise hook material and is bent back into engagement with the adjoining surface 401, formed of loop material, on the straps 40 so as to form a hook and loop (or VELCRO™) type connection. It is to be appreciated, however, that there are numerous other ways for securing the end portion of the headgear strap to itself or to the headgear attachment clip 14 and/or to the headgear attachment tab 24, such as a snap connection, buckle, or locking clamp, as non-limiting examples. The headgear 11 is adjustable, as the straps 40 can be pulled further through the opening 50 of the headgear retaining tab 24 or the elongated opening 130 of the headgear attachment clip 14 to accommodate smaller diameter head sizes.

In addition, in another embodiment, a more permanent attachment of the end portion of the headgear strap 40 to the headgear strap retaining tabs 24 or the headgear attachment clips 14 may be provided. For example, once the patient/user 27 sets the headgear strap 40 to the desired length and threaded in through the elongated opening 50 of the headgear strap retaining tabs 24 or the elongated opening 130 of the headgear attachment clips 14, the free end of the strap 40 can be permanently fixed back onto the strap 40, such as by gluing, sewing, or riveting the overlapping straps together. The straps 40 of the headgear assembly 11 may be elastic or inelastic, and may extend around the back of the head of the patient 27 to secure the mask body 12 on the patient 27, with the flexible peripheral seal structure 20 in sealing engagement with the patient's face.

The mask, as shown in FIG. 1, is a total face mask that accommodates substantially the entire facial area (including the nose, the mouth and the eyes) of the patient. It is to be understood, however, that the present invention also contemplates an oral/nasal mask that accommodates only the mouth and the nose of a user. The configuration of the mask may vary and is not limited to a particular size or configuration, as patients may range in age, size, and/or medical purpose so as to require appropriate selection from among a variety of different mask sizes and configurations as would be appreciated by one skilled in the art. In one embodiment, the size of the face mask is embossed on the lower end portion of the flexible peripheral seal structure 20 as shown by 600 in FIG. 13.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A mask assembly kit for providing gas to a patient, comprising:
   (a) a mask body having an opening defined therein for reception of the gas, the mask body comprising:
      (1) a seal structure structured to sealingly engage with a face of the patient and to surround at least a nose and a mouth of the patient, and
      (2) a connecting portion;
   (b) a first elbow connector, the first elbow connector being valveless; and
   (c) a second elbow connector containing a valve, wherein each of the first elbow connector and the second elbow connector comprises:
      (1) a first connector portion adapted to connect with the connecting portion of the mask body, and
      (2) a second connector portion adapted to connect with a tubing, wherein the connecting portion of the mask body is constructed and arranged to be selectively attached to the first connector portion of either the first elbow connector or the second elbow connector.

2. The mask assembly kit according to claim 1, wherein each first connector portion is constructed and arranged to form a friction fit connection with the connecting portion of the mask.

3. The mask assembly kit according to claim 1, wherein the connecting portion of the mask body and the first connector portion of each of the first and the second elbow connectors forms a rotatable connection.

4. The mask assembly kit according to claim 1, wherein the second elbow connector comprises a plurality of openings that provide gas communication between the patient and atmosphere.

5. The mask assembly kit according to claim 1, wherein the mask body further includes at least one headgear attachment clip.

6. The mask assembly kit according to claim 1, wherein the second elbow connector includes an opening defined between the first connector portion and the second connector portion, and wherein the valve in the second elbow connector is movable between a first position sealing the opening and a second position substantially blocking the opening.

7. The mask assembly according to claim 6, wherein the valve comprises a flexible member that block the opening upon application of pressurized gas in the second elbow connector.

8. The mask assembly kit according to claim 1, further comprising a third elbow connector having a first connector portion adapted to connect with the connecting portion of the mask body, and a second connector portion adapted to connect with a tubing, wherein the connecting portion of the mask body is constructed and arranged to be selectively attached to the first connector portion of either the first elbow connector, the second elbow connector, or the third elbow connector, and wherein the third elbow connector includes a bronchoscope port defined between the first connector portion and the second connector portion.

9. A method or providing a flow of gas to an airway of a patient comprising:
 (a) providing a mask assembly kit for providing gas to a patient, comprising:
  (1) a mask body having an opening defined therein for reception of the gas, the mask body comprising:
   (i) a seal structure structured to sealingly engage with a face of the patient and to surround at least a nose and a mouth of the patient, and
   (i) a connecting portion;
  (2) a first elbow connector, the first elbow connector being valveless; and
  (3) a second elbow connector containing a valve, wherein each of the first elbow connector and the second elbow connector comprises:
   (i) a first connector portion adapted to connect with the connecting portion of the mask body, and
   (ii) a second connector portion adapted to connect with a tubing, wherein the connecting portion of the mask body is constructed and arranged to be selectively attached to the first connector portion of either the first elbow connector or the second elbow connector;
 (b) selecting either the first elbow connector or the second elbow connector; and
 (c) coupling the first connector portion of the selected first or second elbow connector to the connecting portion of the mask body.

10. The method of claim 9, further comprising
 (a) providing a third elbow connector having a first connector portion adapted to connect with the connecting portion of the mask body, a second connector portion adapted to connect with a tubing, and a bronchoscope port defined between the first connector portion and the second connector portion;
 (b) selecting either the first elbow connector, the second elbow connector, or the third elbow connector; and
 (c) coupling the first connector portion of the selected first, second, or third elbow connector to the connecting portion of the mask body.

* * * * *